United States Patent
Kuchimaru

(10) Patent No.: US 8,936,546 B2
(45) Date of Patent: *Jan. 20, 2015

(54) ENDOSCOPIC IMAGE PICKUP UNIT

(71) Applicant: Olympus Medical Systems Corp., Tokyo (JP)

(72) Inventor: Toru Kuchimaru, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 223 days.

This patent is subject to a terminal disclaimer.

(21) Appl. No.: 13/722,104

(22) Filed: Dec. 20, 2012

(65) Prior Publication Data

US 2013/0107025 A1 May 2, 2013

Related U.S. Application Data

(63) Continuation of application No. 12/551,826, filed on Sep. 1, 2009, now Pat. No. 8,360,965.

(30) Foreign Application Priority Data

Sep. 8, 2008 (JP) ................................ 2008-230023

(51) Int. Cl.
    *A61B 1/06* (2006.01)
    *H04N 7/18* (2006.01)
    (Continued)

(52) U.S. Cl.
    CPC ............ *H04N 7/183* (2013.01); *A61B 1/00096* (2013.01); *A61B 1/00101* (2013.01); *A61B 1/0011* (2013.01); *A61B 1/00188* (2013.01);
    (Continued)

(58) Field of Classification Search
    USPC .......... 600/167, 168, 139, 172; 359/379–380, 359/383, 823
    See application file for complete search history.

(56) References Cited

U.S. PATENT DOCUMENTS

| 4,777,524 A | 10/1988 | Nakajima et al. |
| 5,016,993 A | 5/1991 | Akitake |

(Continued)

FOREIGN PATENT DOCUMENTS

| JP | 2003-230532 | 8/2003 |
| JP | 2006-187547 A | 7/2006 |
| JP | 2007-229155 | 9/2007 |

OTHER PUBLICATIONS

Extended European Search Report dated Oct. 23, 2009 issued in corresponding Application No. / Patent No. 09008553.1-1234.

(Continued)

*Primary Examiner* — Anhtuan T Nguyen
*Assistant Examiner* — William Chou
(74) *Attorney, Agent, or Firm* — Scully, Scott, Murphy & Presser, PC

(57) ABSTRACT

An endoscopic image pickup unit includes: a first fixed lens frame which holds a first objective lens group; a second fixed lens frame which, being fitted over the first fixed lens frame, holds a second objective lens group; a movable lens frame which, being installed in the second fixed lens frame so as to be able to move forward and backward along a photographic optical axis, holds a movable lens; and a deformation preventing member which, being interposed between a distal end body and the second fixed lens frame, prevents the second fixed lens frame from being deformed by fixing force of the fixing member when the endoscopic image pickup unit is fixed to the distal end body.

7 Claims, 20 Drawing Sheets

(51) Int. Cl.
  *A61B 1/00* (2006.01)
  *A61B 1/05* (2006.01)
  *G02B 23/24* (2006.01)
  *H04N 5/225* (2006.01)

(52) U.S. Cl.
  CPC .............. *A61B 1/05* (2013.01); *G02B 23/2415* (2013.01); *G02B 23/2423* (2013.01); *G02B 23/243* (2013.01); *G02B 23/2484* (2013.01); *H04N 5/2254* (2013.01); *H04N 2005/2255* (2013.01)
  USPC ........................... 600/167; 600/168; 600/173

(56) References Cited

U.S. PATENT DOCUMENTS

| | | |
|---|---|---|
| 5,179,934 A | 1/1993 | Nagayoshi et al. |
| 5,490,015 A | 2/1996 | Umeyama et al. |
| 5,547,457 A | 8/1996 | Tsuyuki et al. |
| 5,576,894 A | 11/1996 | Kuwana et al. |
| 5,790,319 A | 8/1998 | Okada et al. |
| 5,876,327 A | 3/1999 | Tsuyuki et al. |
| 6,030,339 A | 2/2000 | Tatsuno et al. |
| 6,117,071 A | 9/2000 | Ito et al. |
| 6,307,678 B2 | 10/2001 | Kosaka et al. |
| 6,409,658 B1 | 6/2002 | Mitsumori |
| 6,422,995 B2 | 7/2002 | Akiba |
| 6,447,447 B1 | 9/2002 | Mitsumori |
| 6,497,652 B2 | 12/2002 | Akiba |
| 6,570,717 B1 | 5/2003 | Tu et al. |
| 6,641,530 B2 | 11/2003 | Mitsumori |
| 6,650,488 B2 | 11/2003 | Onda |
| 6,813,092 B2 | 11/2004 | Yoshida et al. |
| 7,294,102 B2 | 11/2007 | Jones et al. |
| 7,489,358 B2 | 2/2009 | Fuji |
| 7,828,721 B2 | 11/2010 | Kumei et al. |
| 2001/0044571 A1 | 11/2001 | Mitsumori |
| 2004/0097791 A1 | 5/2004 | Tokuda et al. |
| 2005/0143624 A1 | 6/2005 | Iddan |
| 2007/0260113 A1 | 11/2007 | Otawara |

OTHER PUBLICATIONS

Non-Final U.S Office Action dated Dec. 7, 2011 issued in corresponding U.S. Appl. No. 12/551,826.

Final U.S Office Action dated Jun. 18, 2012 issued in corresponding U.S. Appl. No. 12/551,826.

Notice of Allowance and Fee(s) Due dated Oct. 1, 2012 issued in corresponding U.S. Appl. No. 12/551,826.

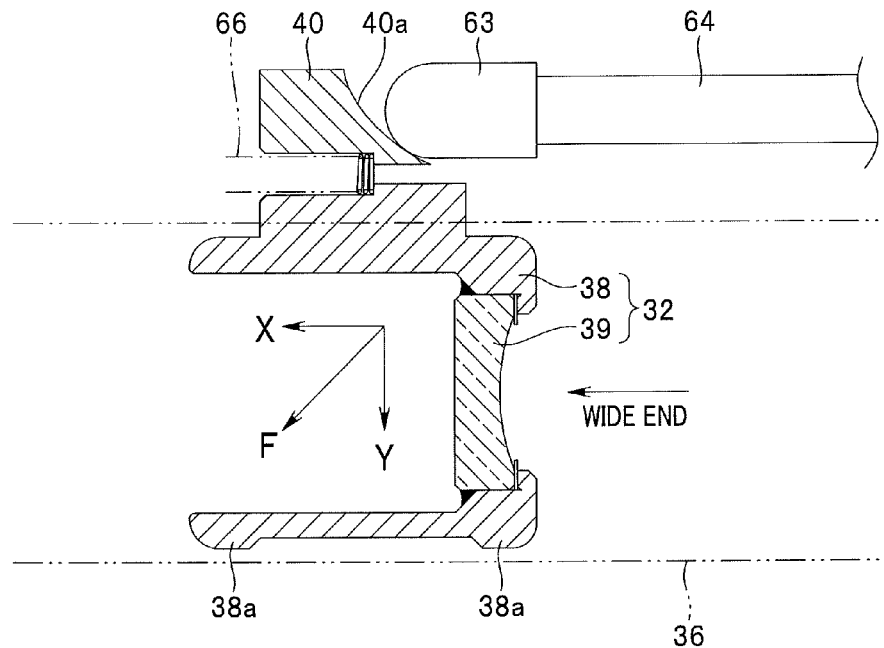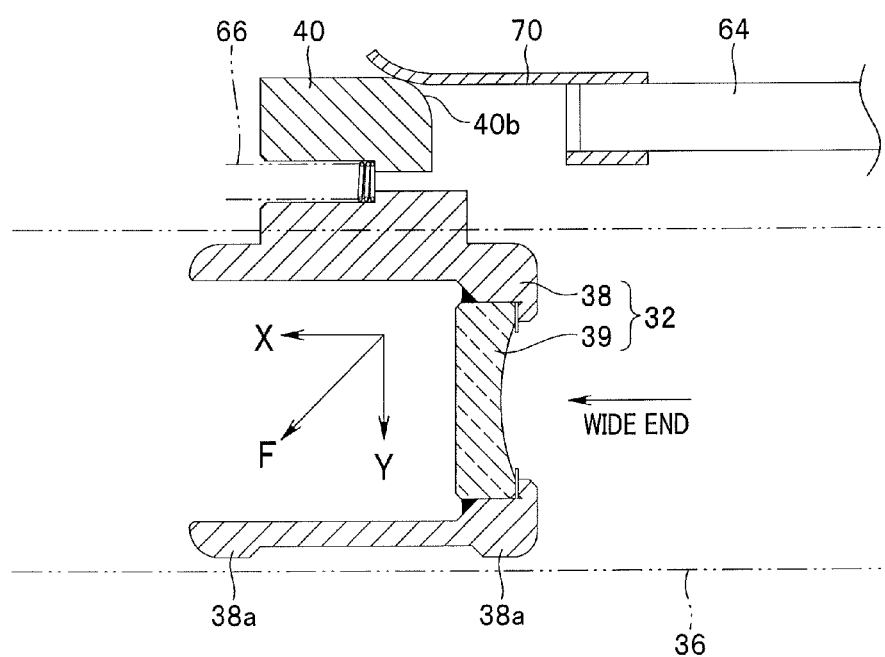

ENDOSCOPIC IMAGE PICKUP UNIT

This application is a Continuation Application of U.S. Ser. No. 12/551,826 filed on Sep. 1, 2009, which claims benefit of Japanese Application No. 2008-230023 filed in Japan on Sep. 8, 2008, the contents of each of which are incorporated by reference.

BACKGROUND OF THE INVENTION

1. Field of the Invention

The present invention relates to an endoscopic image pickup unit which can change optical characteristics of an objective optical system disposed in an endoscope.

2. Description of the Related Art

As is well known, electronic endoscopes are widely used to carry out observations, treatments, and the like in the body (body cavity) of a living organism as well as to carry out inspections, repairs, and the like in industrial plant facilities. Some recent electronic endoscopes use an image pickup unit which can change focal length for a focusing function or zooming function by moving an observation optical system toward a photographic optical axis, where the focusing function is used for focus adjustment and the zooming function is used to switch between a wide zoom and tele zoom.

In relation to an image pickup unit installed in such an endoscope, a technique for changing optical characteristics for a zooming function and the like by moving a movable lens frame forward and backward is disclosed, for example, in Japanese Patent Application Laid-Open Publication No. 2003-230532.

Japanese Patent Application Laid-Open Publication No. 2003-230532 discloses an endoscopic image pickup unit equipped with an objective optical system which has a front-group lens frame, a rear-group lens frame, and a movable lens frame which moves forward and backward along the photographic optical axis in the rear-group lens frame. The conventional image pickup unit is fixed to a distal end body when a fixing screw screwed into the distal end body presses an outer peripheral portion of the objective optical system in a circumferential direction.

Also, for example, Japanese Patent Application Laid-Open Publication No. 2007-229155 discloses an endoscope equipped with an actuator unit which controls forward and backward movements of a movable lens frame using a spring and shape-memory alloy wire.

SUMMARY OF THE INVENTION

The present invention provides an endoscopic image pickup unit which, being fixedly fitted in a distal end body of an endoscope by a fixing member, can change optical characteristics of an objective optical system, the endoscopic image pickup unit including: a first fixed lens frame which holds a first objective lens group; a second fixed lens frame which, being fitted over the first fixed lens frame, holds a second objective lens group; a movable lens frame which, being installed in the second fixed lens frame so as to be able to move forward and backward along a photographic optical axis, holds a movable lens; and a deformation preventing member which, being interposed between the distal end body and the second fixed lens frame, prevents the second fixed lens frame from being deformed by fixing force of the fixing member when the endoscopic image pickup unit is fixed to the distal end body.

The present invention provides an endoscopic image pickup unit which, being fixedly fitted in a distal end body of an endoscope by a fixing member, can change optical characteristics of an objective optical system, the endoscopic image pickup unit including: a first fixed lens frame which holds a first objective lens group; a second fixed lens frame which, being fitted over the first fixed lens frame, holds a second objective lens group; a movable lens frame which, being installed in the second fixed lens frame so as to be able to move forward and backward along a photographic optical axis, holds a movable lens; an urging member which urges the movable lens frame in one direction along the photographic optical axis; an actuator which extends the movable lens frame in the other direction along the photographic optical axis against urging force of the urging member; an abutting member which, being installed on the actuator, abuts the movable lens frame; an abutted portion which, being installed on the movable lens frame, is abutted by the abutting member; and an abutted surface which, being formed on the abutted portion, scatters pressing force applied by the abutting member, in a direction approximately orthogonal to the photographic optical axis.

The above and other objects, features and advantages of the invention will become more clearly understood from the following description referring to the accompanying drawings.

BRIEF DESCRIPTION OF THE DRAWINGS

FIG. 21 is a sectional view showing a movable lens unit located at a wide end position, according to a variation of the embodiment;

FIG. 22 is a sectional view showing a movable lens unit located at a wide end position, according to a variation different from the one in FIG. 21 of the embodiment;

DETAILED DESCRIPTION OF THE PREFERRED EMBODIMENTS

An embodiment of the present invention will be described below with reference to the drawings.

Figure 1:
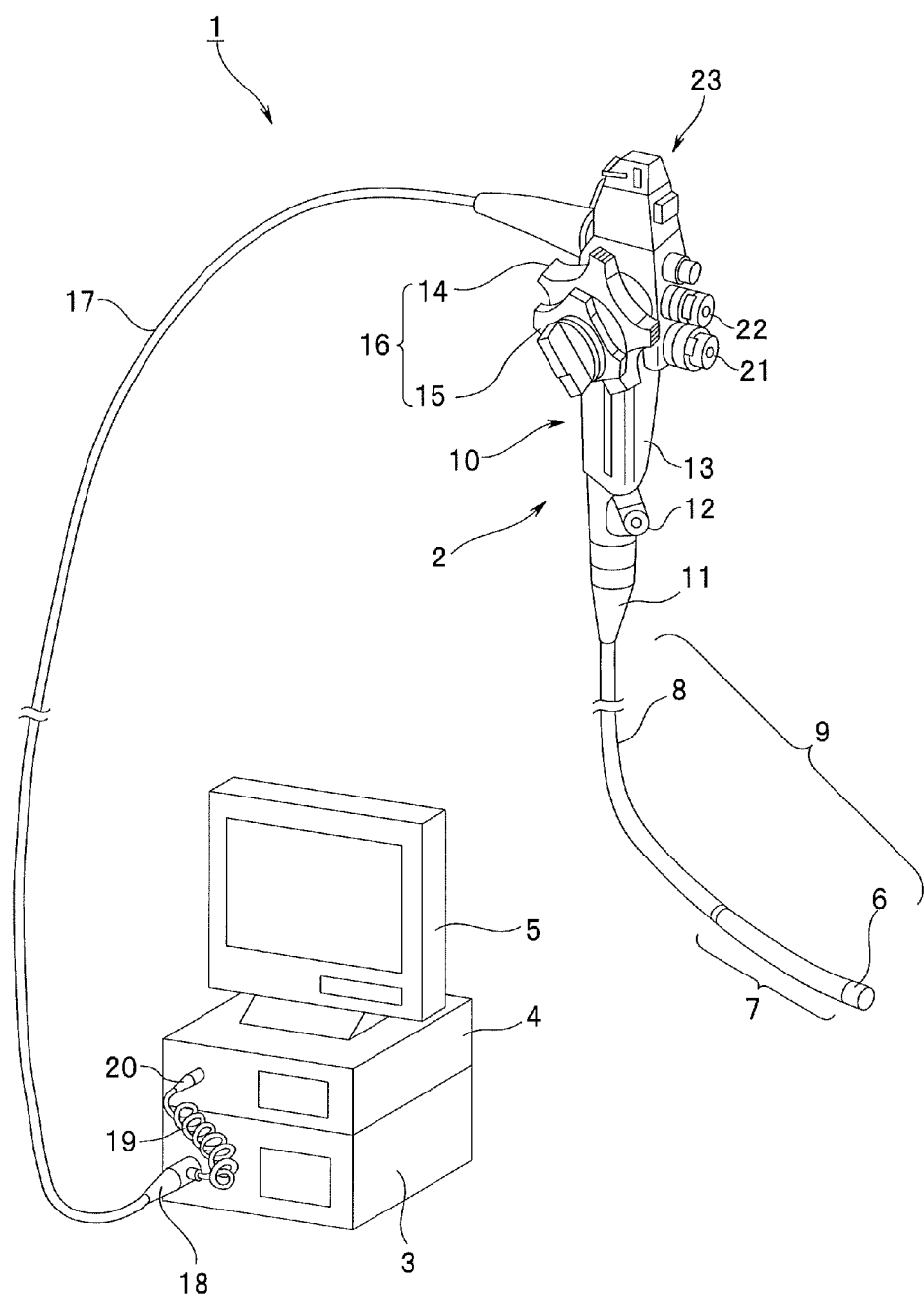
FIG. 1 is a diagram showing an overall configuration of an electronic endoscope system according to one embodiment of the present invention.
Figure 2:
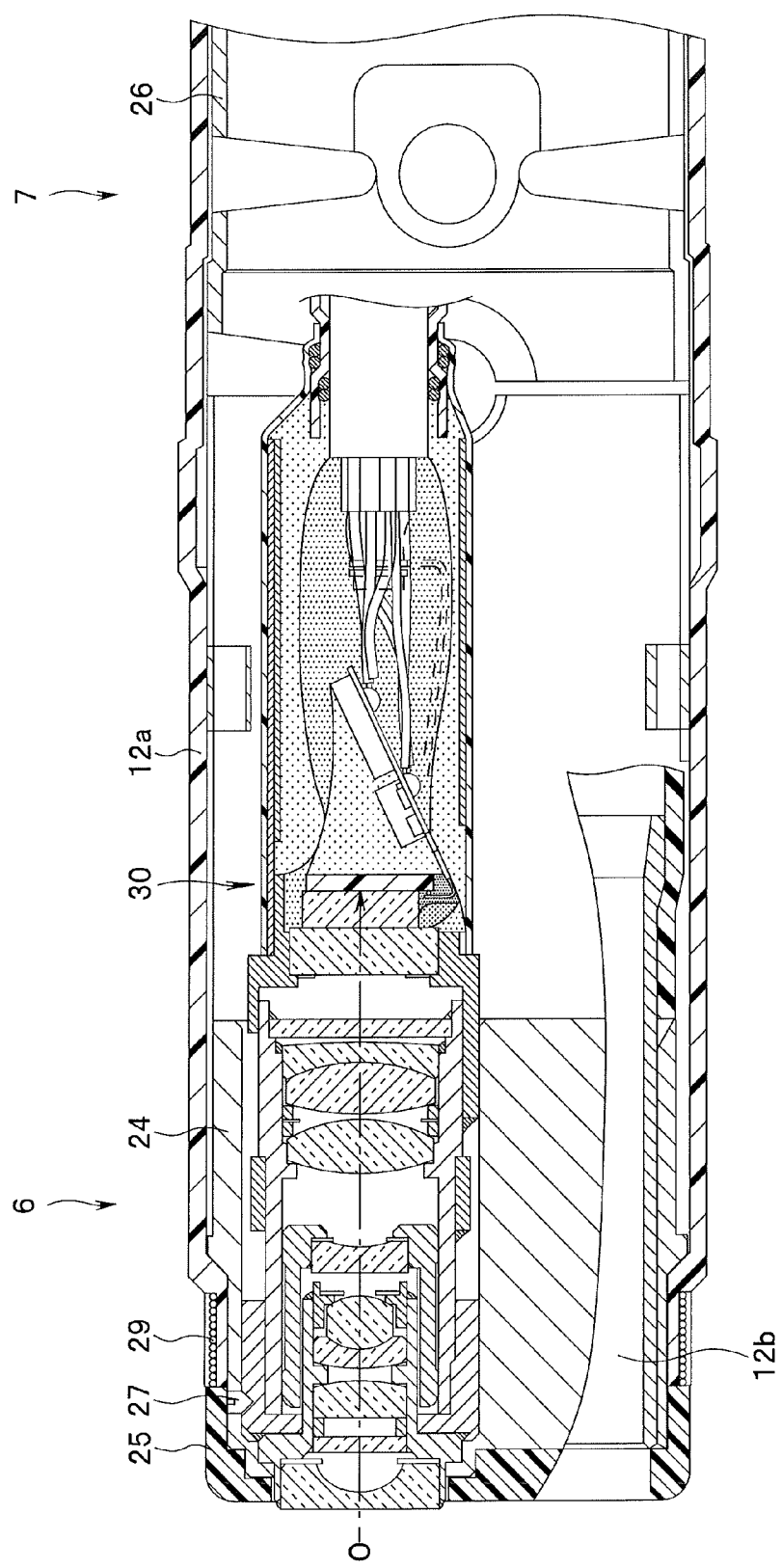
FIG. 2 is a sectional view showing an internal configuration of a distal end portion of the endoscope according to the embodiment of the present invention.
Figure 3:
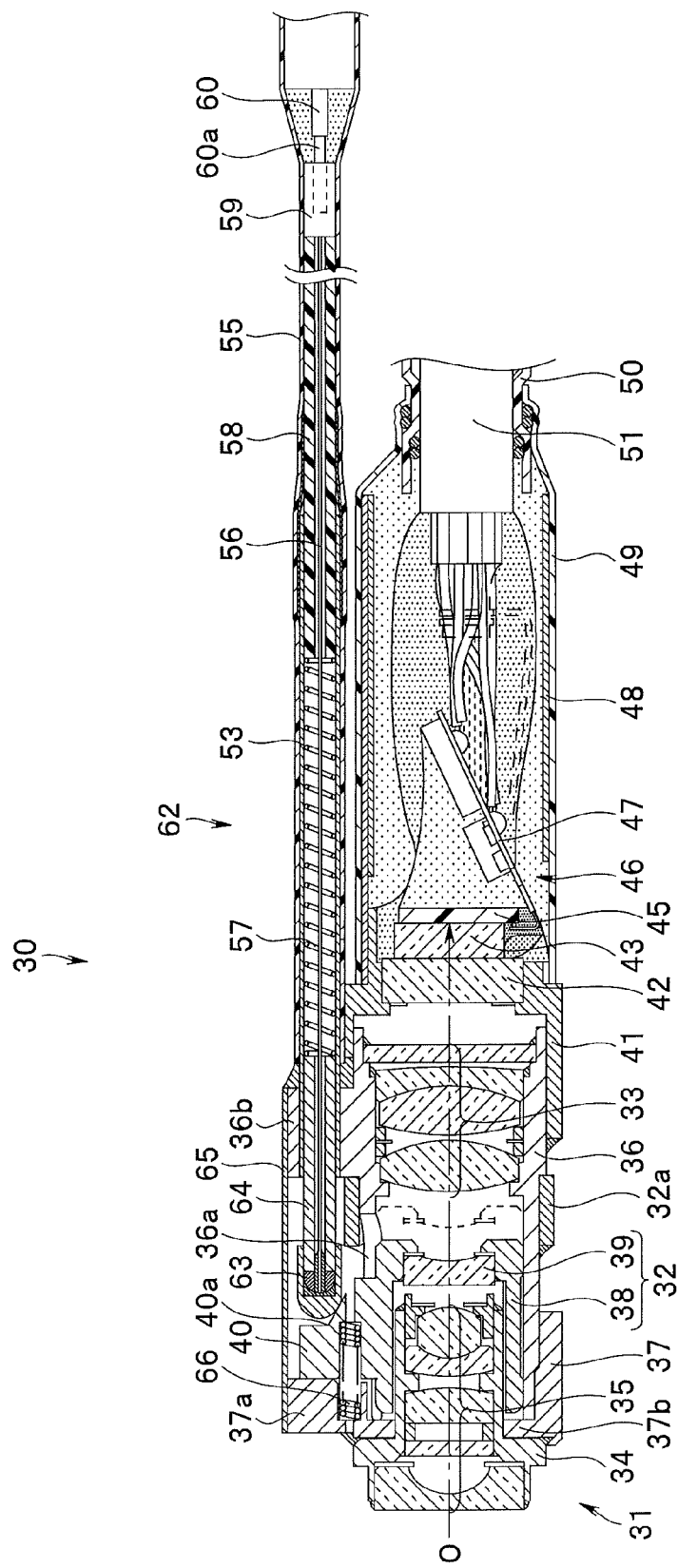
FIG. 3 is a sectional view showing a configuration of an image pickup unit according to the embodiment of the present invention.
Figure 4:
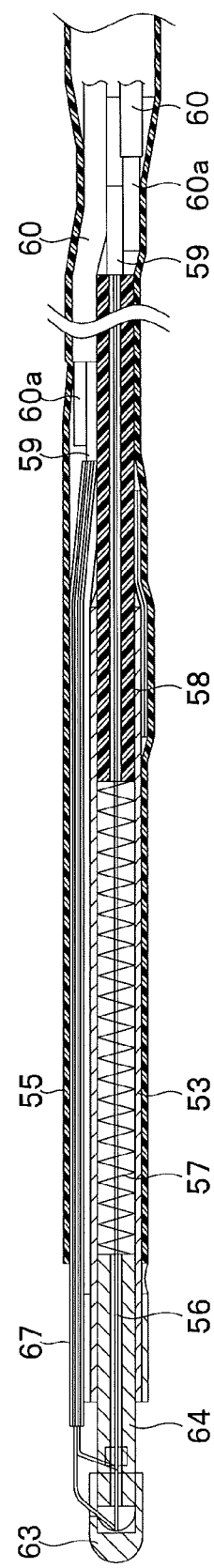
FIG. 4 is a sectional view showing a configuration of an actuator according to the embodiment of the present invention.
Figure 5:
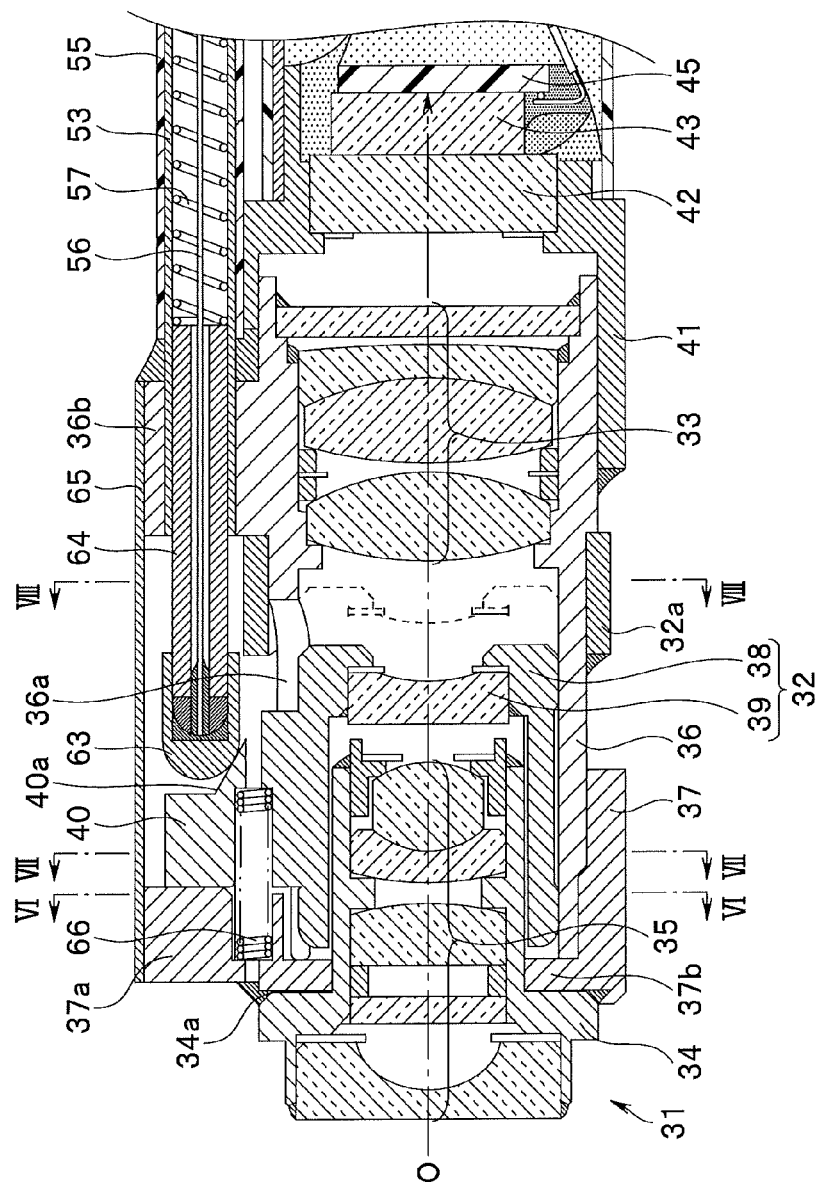
FIG. 5 is a partial sectional view showing the configuration of the image pickup unit according to the embodiment of the present invention.
Figure 6:
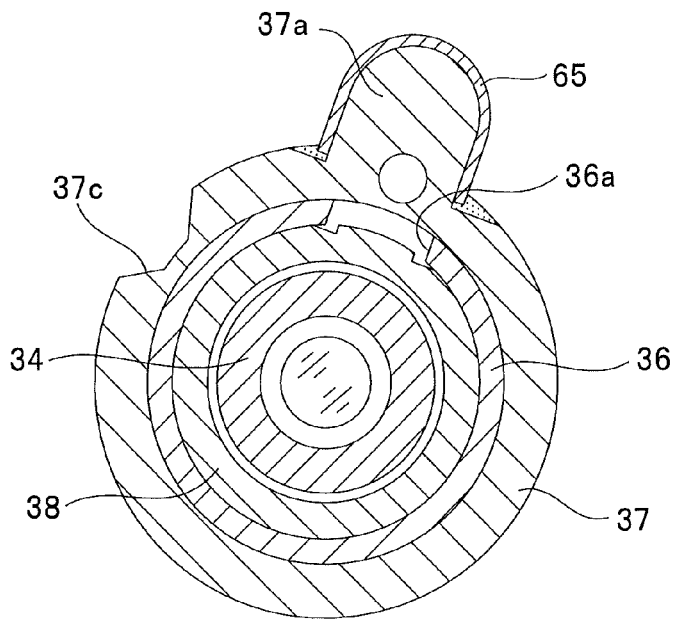
FIG. 6 is a sectional view taken along line VI-VI in FIG. 5, according to the embodiment of the present invention.
Figure 7:
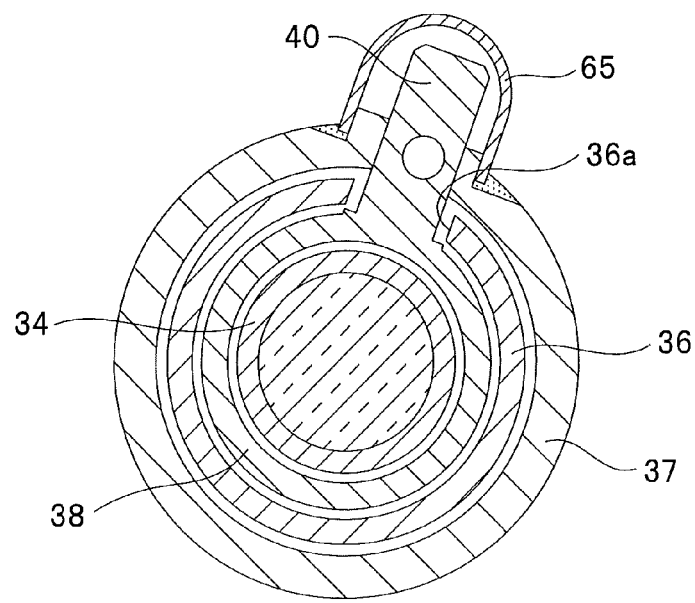
FIG. 7 is a sectional view taken along line VII-VII in FIG. 5, according to the embodiment of the present invention.
Figure 8:
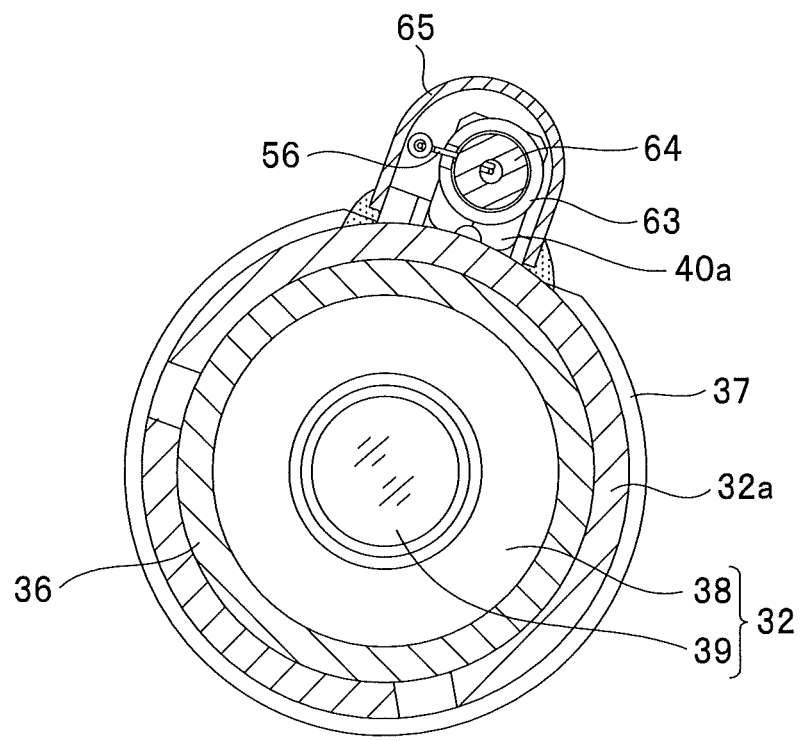
FIG. 8 is a sectional view taken along line VIII-VIII in FIG. 5, according to the embodiment of the present invention.
Figure 9:
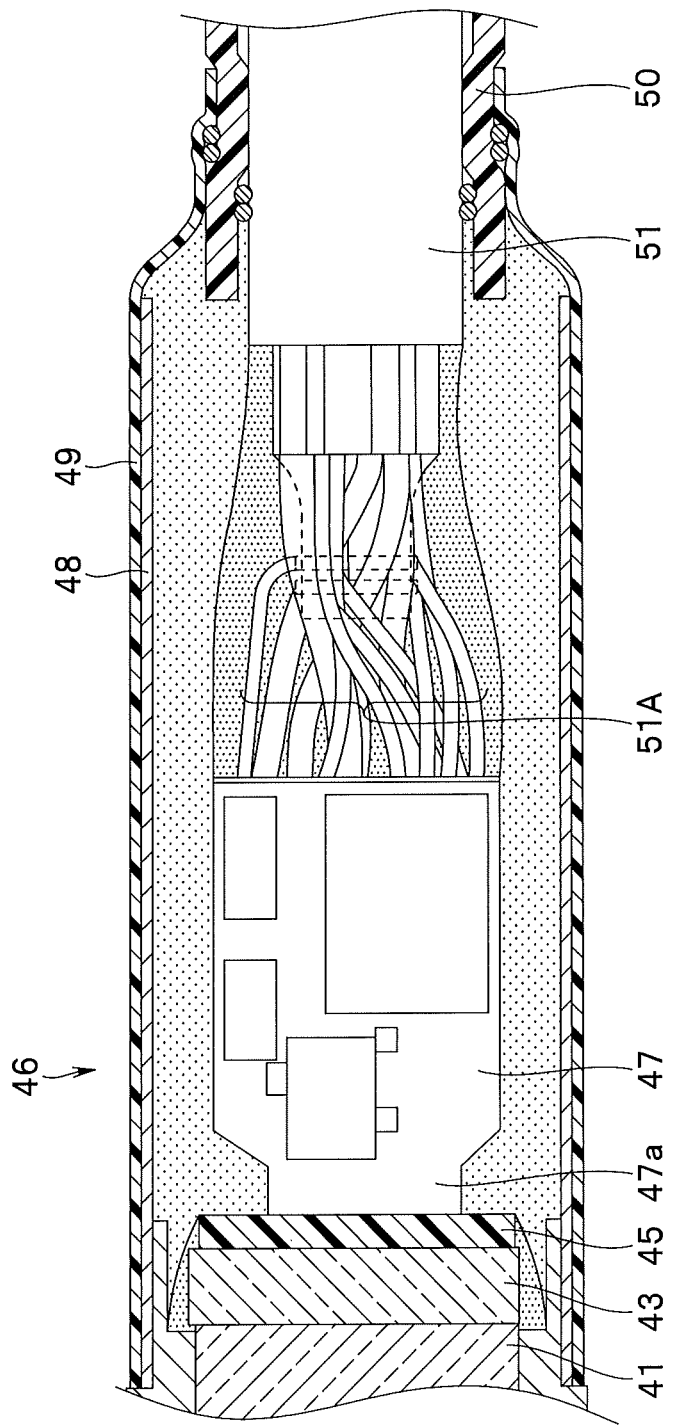
FIG. 9 is a partial sectional view showing a front side of a TAB board according to the embodiment of the present invention.
Figure 10:
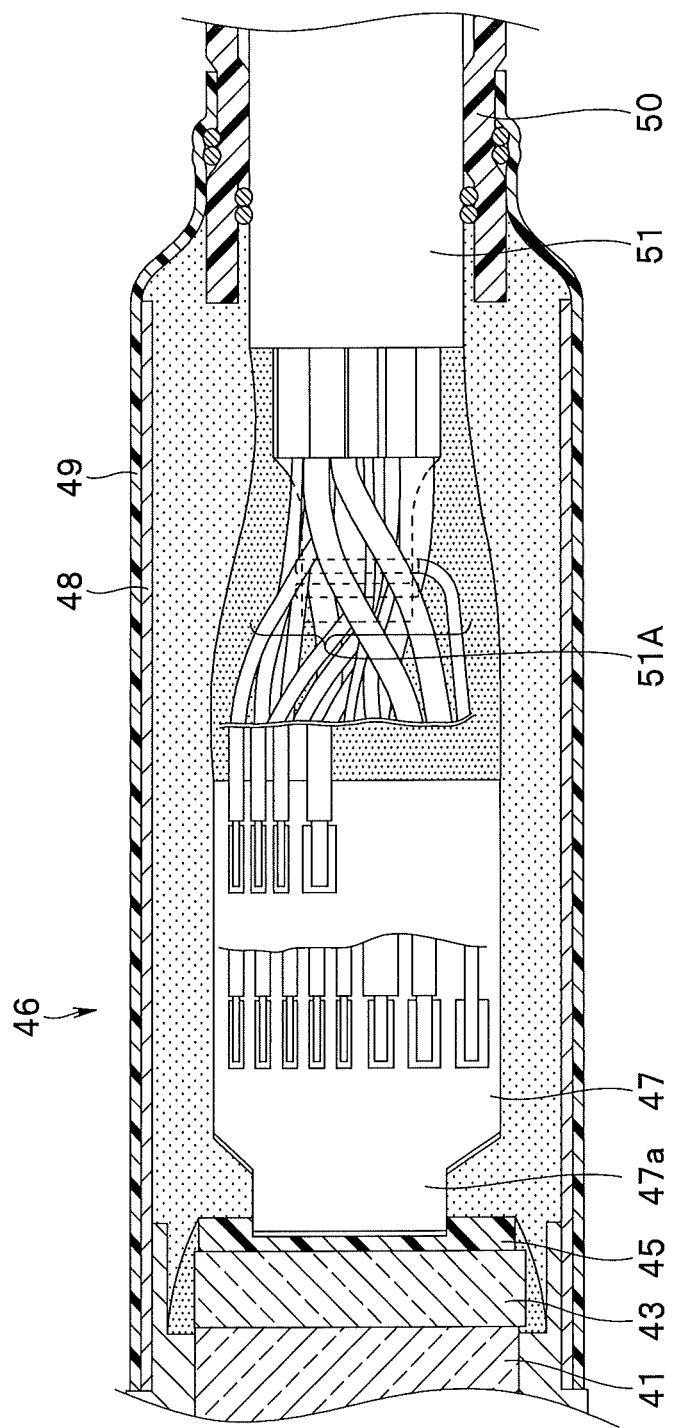
FIG. 10 is a partial sectional view showing a rear side of a TAB board according to the embodiment of the present invention.
Figure 11:
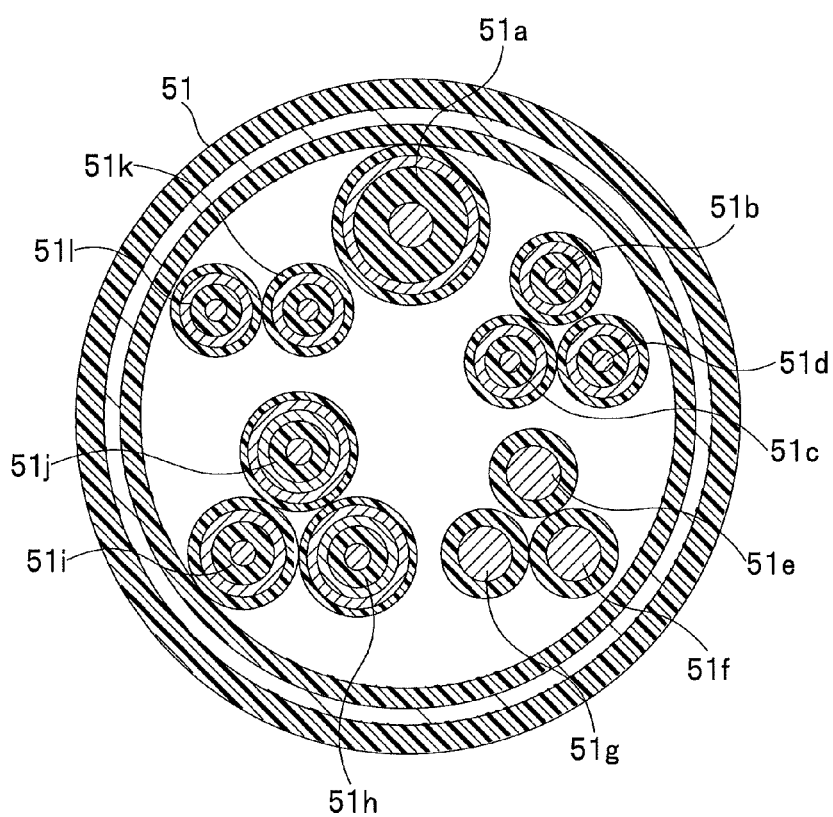
FIG. 11 is a sectional view showing a cable according to the embodiment of the present invention.
Figure 12:
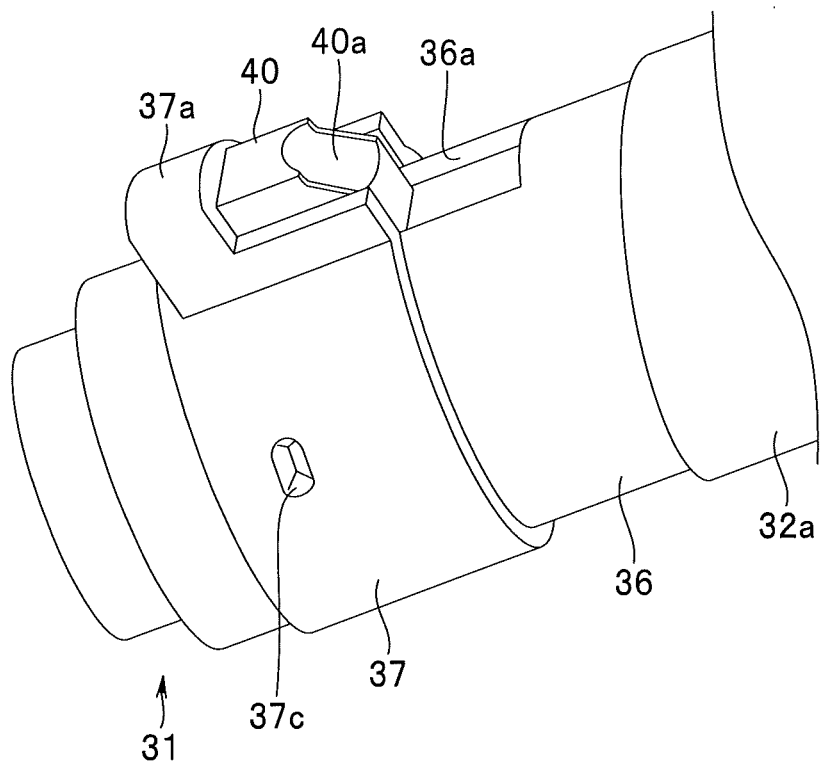
FIG. 12 is a perspective view showing a configuration of the image pickup unit according to the embodiment of the present invention.
Figure 13:
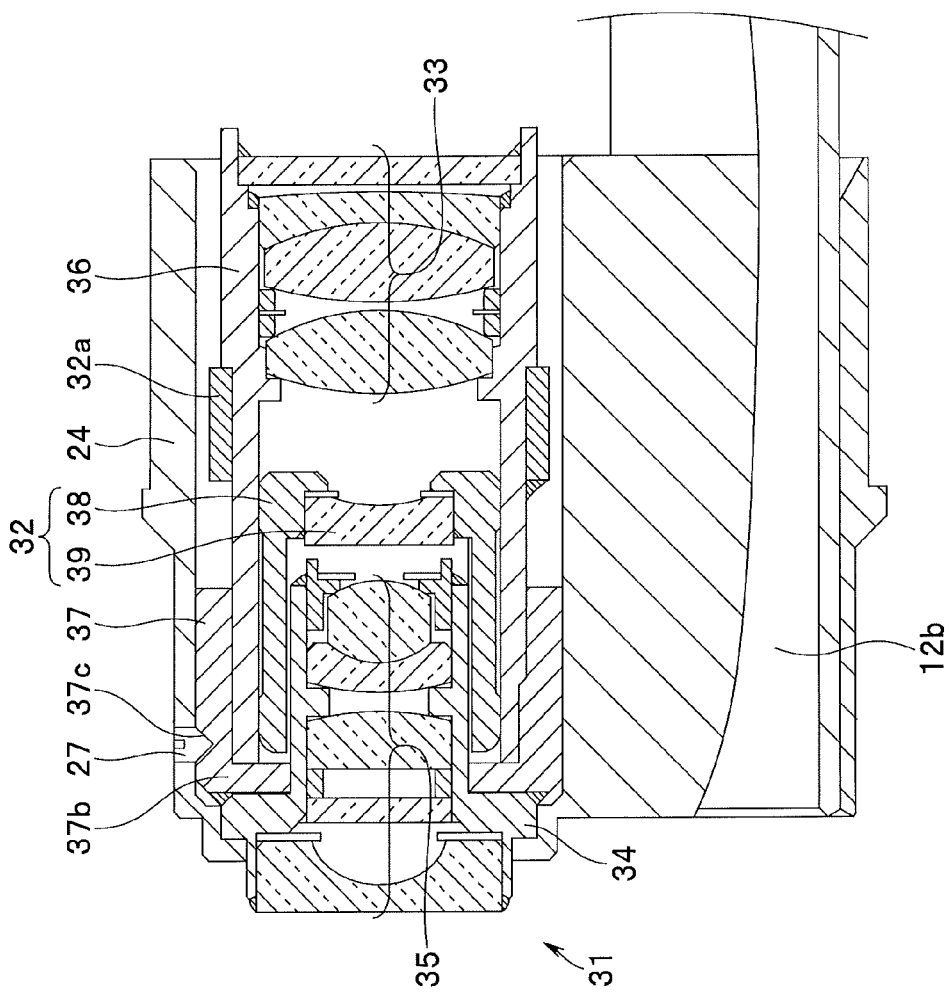
FIG. 13 is a partial sectional view showing a configuration of the image pickup unit according to the embodiment of the present invention.
Figure 14:
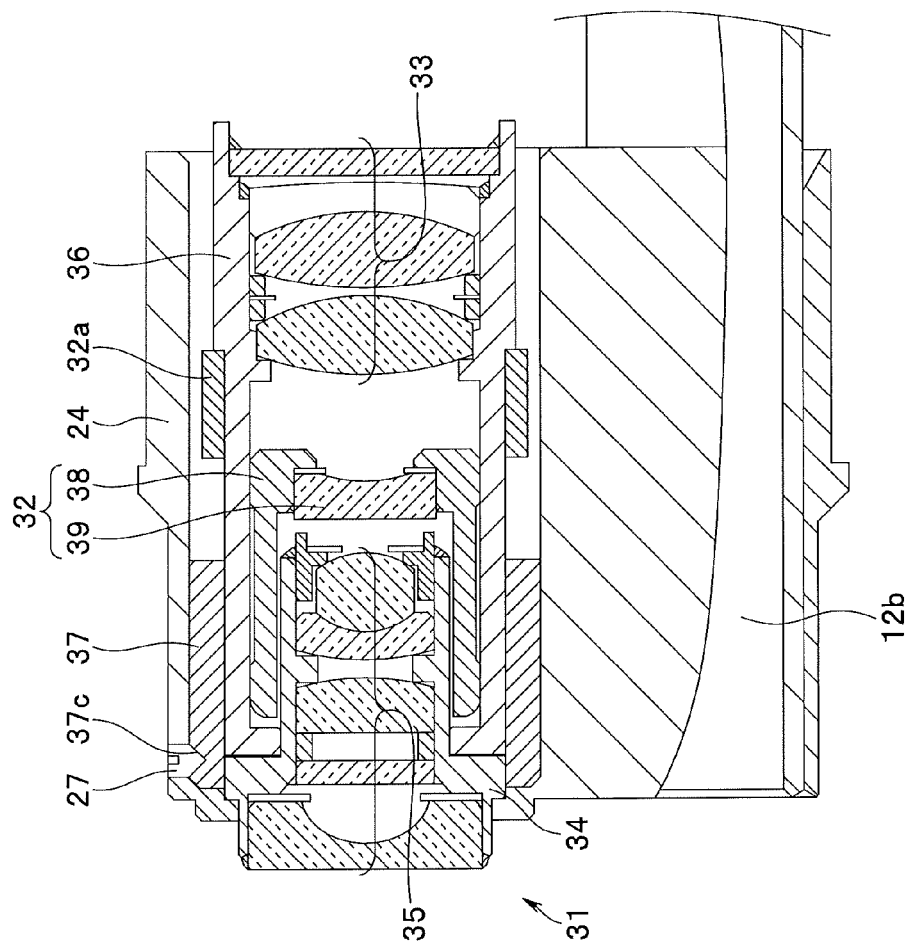
FIG. 14 is a partial sectional view showing a configuration of an image pickup unit according to a variation of the embodiment.
Figure 15:
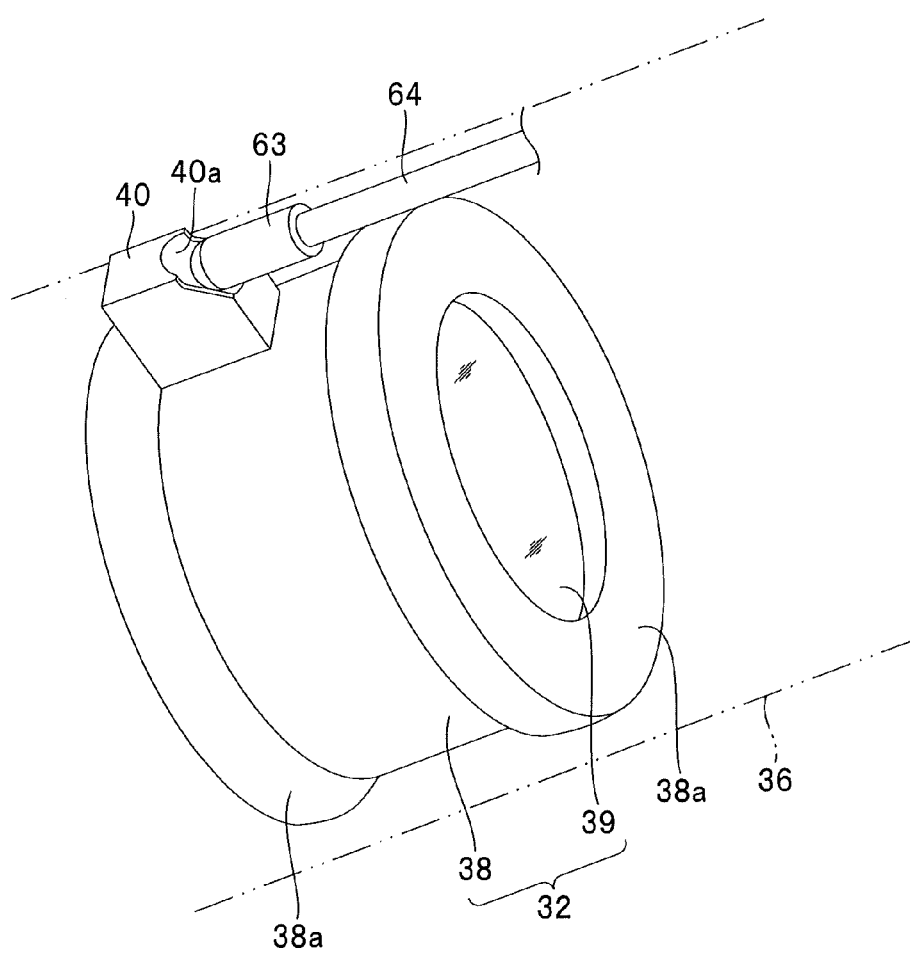
FIG. 15 is a perspective view showing a movable lens unit according to the embodiment of the present invention.
Figure 16:
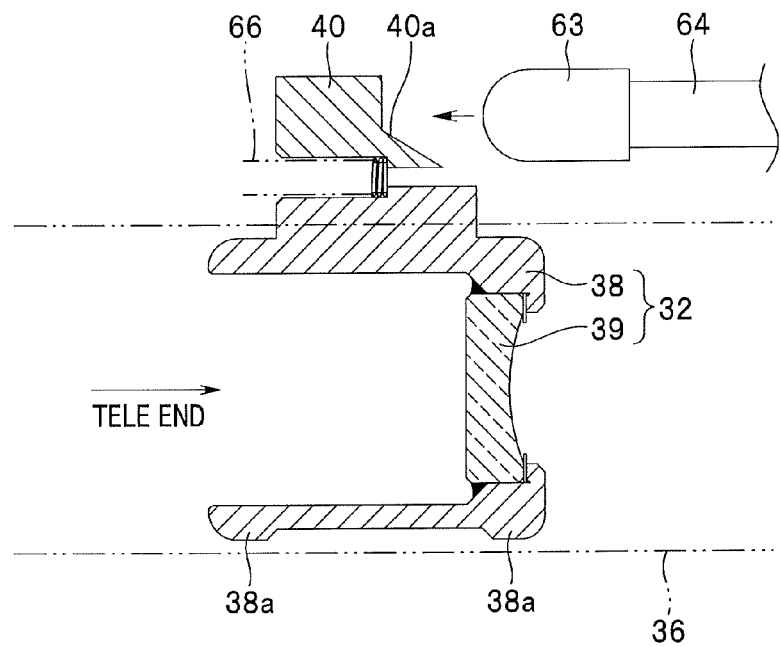
FIG. 16 is sectional view showing the movable lens unit located at a tele end position, according to the embodiment of the present invention.
Figure 17:
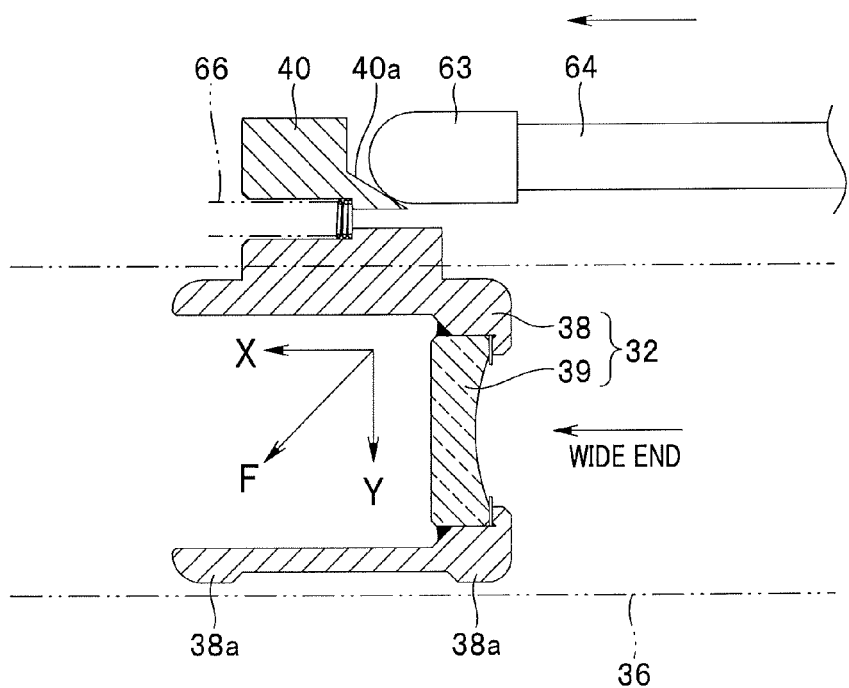
FIG. 17 is a sectional view showing the movable lens unit located at a wide end position, according to the embodiment of the present invention.
Figure 18:
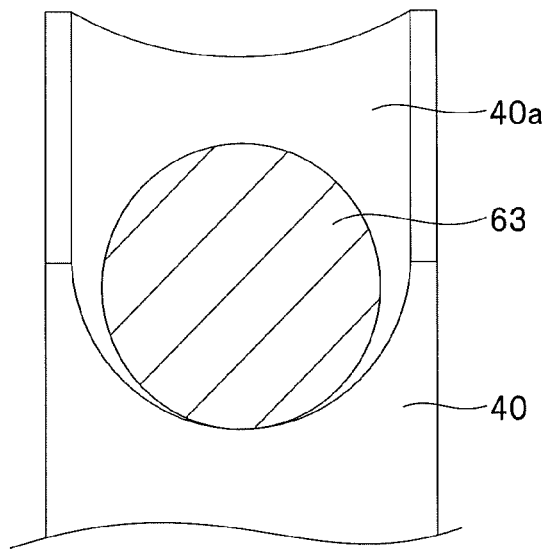
FIG. 18 is a partial sectional view showing an example of a sloping portion of a catcher rod according to the embodiment of the present invention.
Figure 19:
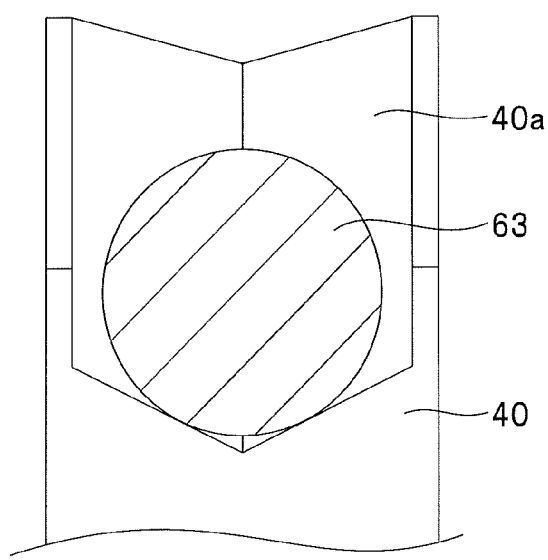
FIG. 19 is a partial sectional view showing an example of a sloping portion of a catcher rod different from the catcher rod in FIG. 18, according to the embodiment of the present invention.
Figure 20:
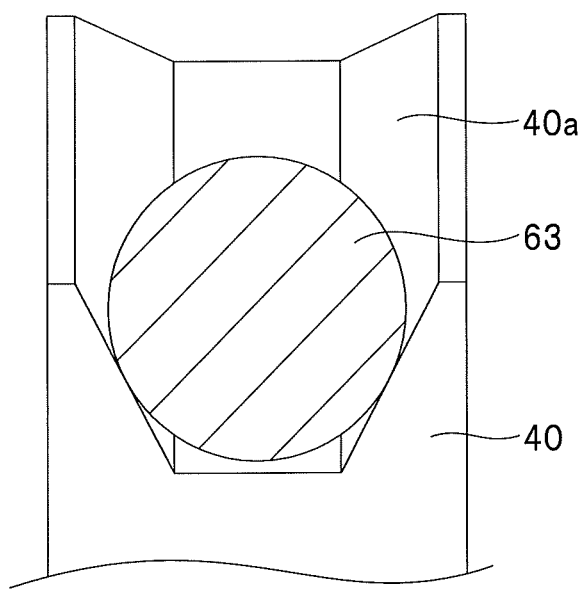
FIG. 20 is a partial sectional view showing an example of a sloping portion of a catcher rod different from the catcher rods in FIGS. 18 and 19, according to the embodiment of the present invention.
Figure 23:
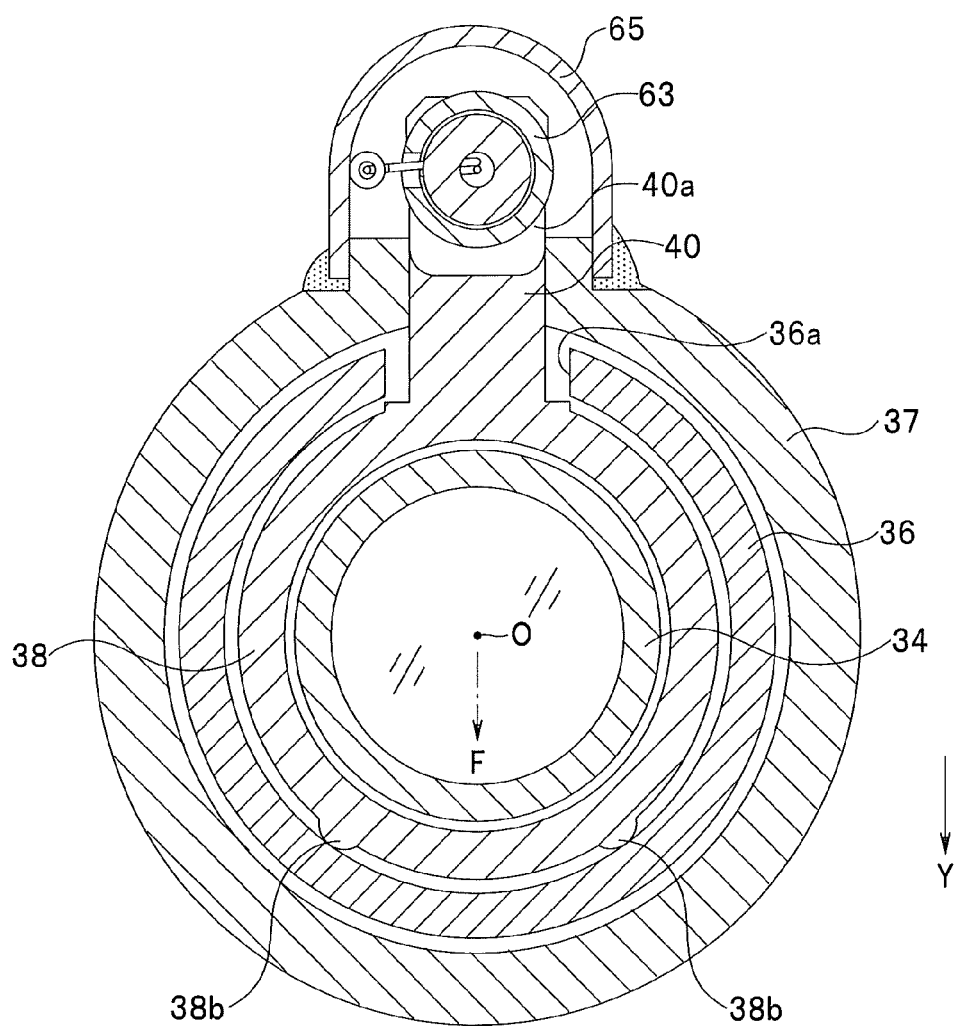
FIG. 23 is a cross sectional view of the image pickup unit, showing an exemplary configuration of the movable lens unit according to the embodiment of the present invention.
Figure 24:
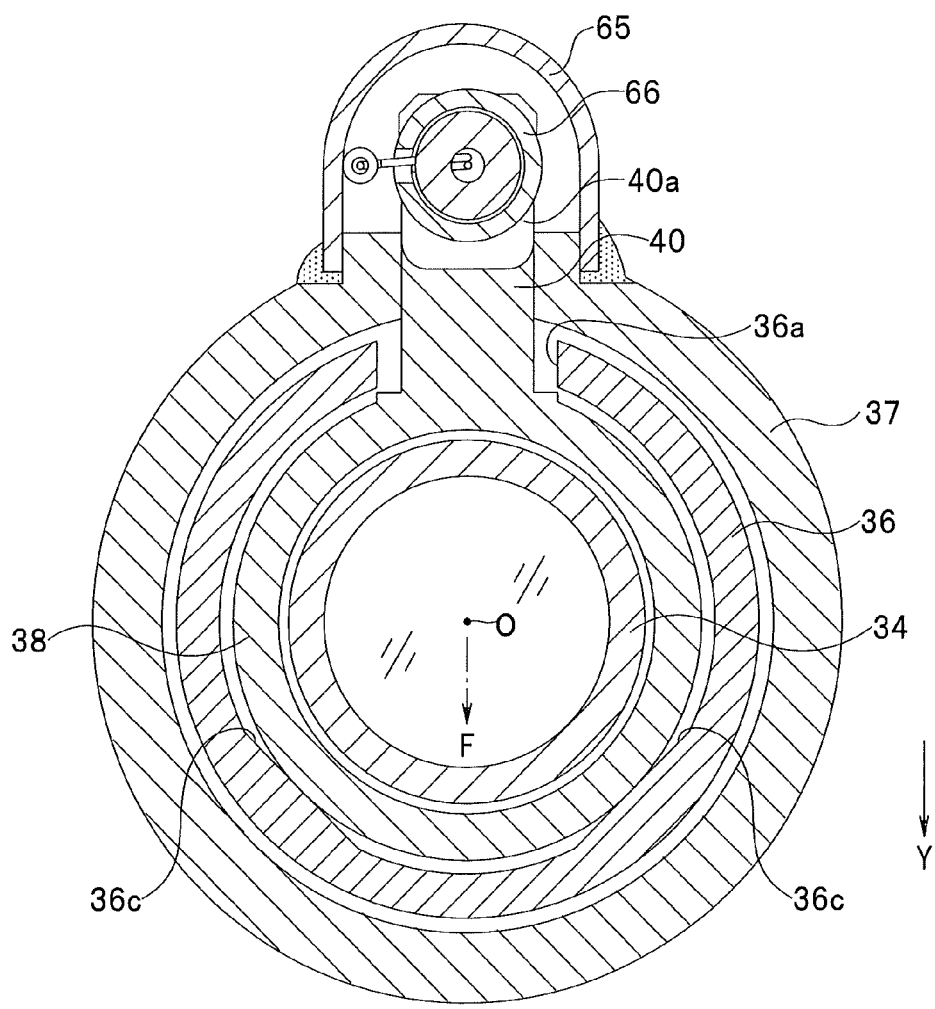
FIG. 24 is a cross sectional view of the image pickup unit, showing an exemplary configuration of the rear lens group frame unit according to the embodiment of the present invention.

First, the present invention will be described below with reference to FIGS. 1 to 24. FIGS. 1 to 24 concerns the embodiment of the present invention, where FIG. 1 is a diagram showing an overall configuration of an electronic endoscope system; FIG. 2 is a sectional view showing an internal configuration of a distal end portion of the endoscope; FIG. 3 is a sectional view showing a configuration of an image pickup unit; FIG. 4 is a sectional view showing a configuration of an actuator; FIG. 5 is a partial sectional view showing the configuration of the image pickup unit; FIG. 6 is a sectional view taken along line VI-VI in FIG. 5; FIG. 7 is a sectional view taken along line VII-VII in FIG. 5; FIG. 8 is a sectional view taken along line VIII-VIII in FIG. 5; FIG. 9 is a partial sectional view showing a front side of a TAB board; FIG. 10 is a partial sectional view showing a rear side of a TAB board; FIG. 11 is a sectional view showing a cable; FIG. 12 is a perspective view showing a configuration of the image pickup unit; FIG. 13 is a partial sectional view showing a configuration of the image pickup unit; FIG. 14 is a partial sectional view showing a configuration of an image pickup unit according to a variation; FIG. 15 is a perspective view showing a movable lens unit; FIG. 16 is sectional view showing the movable lens unit located at a tele end position; FIG. 17 is a sectional view showing the movable lens unit located at a wide end position; FIG. 18 is a partial sectional view showing an example of a sloping portion of a catcher rod; FIG. 19 is a partial sectional view showing an example of a sloping portion of a catcher rod different from the catcher rod in FIG. 18; FIG. 20 is a partial sectional view showing an example of a sloping portion of a catcher rod different from the catcher rods in FIGS. 18 and 19; FIG. 21 is a sectional view showing a movable lens unit located at a wide end position, according to a variation; FIG. 22 is a sectional view showing a movable lens unit located at a wide end position, according to a variation different from the one in FIG. 21; FIG. 23 is a cross sectional view of the image pickup unit, showing an exemplary configuration of the movable lens unit; and FIG. 24 is a cross sectional view of the image pickup unit, showing an exemplary configuration of the rear lens group frame.

As shown in FIG. 1, an electronic endoscope system (hereinafter simply referred to as an endoscope system) 1 according to the present embodiment includes an electronic endoscope apparatus (hereinafter simply referred to as an endoscope) 2, light source device 3, video processor 4, and color monitor 5, all of which are electrically interconnected.

The endoscope 2 includes an insertion portion 9 and an operation portion 10 extending from the insertion portion 9. A universal cord 17 which extends from the operation portion 10 is connected to the light source device 3 via a scope connector 18. Also, a coiled scope cable 19 extends from the scope connector 18. The other end of the scope cable 19 is provided with an electrical connector 20, which in turn is connected to the video processor 4.

Starting from a distal end, the insertion portion 9 includes a distal end portion 6, a bending portion 7, and a flexible tubular portion 8, all of which are installed in a linked manner. In a distal end face of the distal end portion 6, there are a distal opening portion, an observation window, multiple illumination windows, an observation window cleaning port, and an observed-object cleaning port (none is shown).

Behind the observation window, an image pickup unit (described later) is incorporated in the distal end portion 6. Behind the multiple illumination windows, is a light guide bundle which, being passed through the universal cord 17 by entering from the distal end portion 6, transmits light from the light source device 3.

An observation window cleaning nozzle (not shown) is installed in the distal end portion 6. The observation window cleaning nozzle constitutes an opening portion of cleaning tubes (not shown) which are inserted into the universal cord 17 through the distal end portion 6. The cleaning tubes are connected to a cleaning tank and a compressor (none is shown) on the side of the light source device 3, where the cleaning tank stores cleaning water.

The operation portion 10 includes a bend preventing portion 11 from which the insertion portion 9 extends, a forceps port 12 disposed in a flank of lower part, an operation portion body 13 which constitutes a gripping portion in a mid-portion, a bending operation portion 16 made up of two bending operation knobs 14 and 15 installed in upper part, an air/water supply control portion 21, a suction control portion 22, and a plurality of switching portions 23 made up of multiple switches and used to operate image pickup functions (e.g., zooming function). Incidentally, the forceps port 12 in the operation portion 10 constitutes an opening portion of a treatment instrument channel (not shown) which is formed by passing through the insertion portion 9 to the distal opening portion of the distal end portion 6.

Next, mainly a configuration of the distal end portion 6 of the endoscope 2 will be described below with reference to FIG. 2.

As shown in FIG. 2, an image pickup unit 30 is disposed in the distal end portion 6. The image pickup unit 30 is fitted into a distal rigid member 24 which is a rigid distal end body and fixed firmly to the distal rigid member 24 at a flank using a setscrew 27 which is a fixing member in conjunction with an adhesive. A distal cover 25 which constitutes the distal end face of the distal end portion 6 is fixedly bonded to cover distal part of the distal rigid member 24.

The distal opening portion which is a hole formed in the distal cover 25 constitutes an opening portion of the treatment instrument channel 12b in the distal end portion 6. Besides, a distal insertion portion covering member 12a made of rubber is installed to integrally cover an outer periphery of the distal rigid member 24 and bending pieces 26 in the bending portion 7 so as to form outer shape of the distal end portion 6 and bending portion 7. An outer peripheral portion of a distal end of the distal insertion portion covering member 12a is fixed to the distal end portion 6 via a thread-bonded portion 29.

In addition to the treatment instrument channel 12b and the image pickup unit 30, the following members (none is shown) are disposed in the distal rigid member 24: the light guide bundle which guides illumination light, the observation window cleaning nozzle used to clean the observation window in the distal end portion 6 and supply air to a body cavity, a conduit communicated with the cleaning tubes, and an angle wire used to operate the bending portion 7.

The observation window cleaning nozzle, the cleaning tube, the light guide bundle, the angle wire, and other members have known configuration, and thus detailed description thereof will be omitted.

Next, a configuration of the image pickup unit 30 will be described in detail below with reference to FIGS. 3 to 10.

The image pickup unit 30 according to the present embodiment is configured such that inner lenses can be moved forward and backward to change focal length and thereby change optical characteristics for a focusing function (focus adjustment) or zooming function. In the present embodiment, the zooming function which switches between Wide and Tele will be described as an example of a function which is achieved by changing the focal length through forward and backward movements of the inner lenses and thereby changing optical magnification. As described later, optical characteristics of the image pickup unit 30 are configured such that a stop after forward movement of a movable lens unit 32 will set wide mode and that a stop after backward movement will set tele mode.

As shown in FIG. 3, starting from the distal end, the image pickup unit 30 mainly includes a front lens group frame 34 which holds a front lens group 35, a rear lens group frame 36 which holds a rear lens group 33, a movable lens frame 38 which, being installed between the lens groups 35 and 33, holds a movable lens 39, forming outer shape of the movable lens unit 32, and a solid-state image pickup device unit 46 which includes, for example, a CCD and CMOS, where the front lens group frame 34 is a first fixed lens frame, the front lens group 35 is a first lens group which constitutes a front lens group unit 31 and contains multiple objective lenses, the rear lens group frame 36 is a second fixed lens frame, the rear lens group 33 is a second lens group which contains multiple objective lenses, and the movable lens unit 32 is a movable body. Incidentally, the rear lens group 33 and rear lens group frame 36 make up a rear lens group unit which is a second fixed lens unit.

In the image pickup unit 30, a proximal end portion of the front lens group frame 34 and distal end portion of the rear lens group frame 36 are joined by fitting. A screw receiving tube 37 which is a tubular body serving as a deformation preventing member for the rear lens group frame 36 is fixedly fitted around an outer peripheral portion of the distal end portion of the rear lens group frame, being sandwiched between the front lens group frame 34 and rear lens group frame 36.

The screw receiving tube 37 extends upward (as viewed in the figures) and has a restricting portion 37a which restricts forward movement of the movable lens unit 32 by abutting the movable lens unit 32 and a rib 37b which is shaped like an inward flange and formed on a distal side, extending radially inward. The front lens group frame 34 is fitted into the rib 37b such that the rib 37b will abut an outer peripheral portion of the front lens group frame 34.

In the image pickup unit 30 according to the present embodiment, for fine tuning of optical settings including focus adjustments and field-of-view adjustments, one or more thin sheets 34a, for example, 50 μm each in thickness are installed between the front lens group unit 31 and screw receiving tube 37 (see FIG. 5).

Also, a proximal end portion of the rear lens group frame 36 is fixedly inserted in a distal part of a solid-state image pickup device holding frame 41 which holds the solid-state image pickup device unit 46. That is, the solid-state image pickup device holding frame 41 is fitted over the rear lens group frame 36. This configuration makes it possible to grip rigid part during focus adjustments at assembly time, eliminating the need to grip shielded sides of the solid-state image pickup device unit 46. This in turn makes it possible to reduce degradation of optical performance such as an increased deflection angle. That is, variations in the deflection angle are reduced during focus adjustments when the solid-state image pickup device holding frame 41 is fitted over the rear lens group frame 36. This makes it possible to reduce blur in upper part of images.

Behind the front lens group unit 31, the movable lens unit 32 is installed slidably along a photographic optical axis O in the rear lens group frame 36. A catcher rod 40 which is an abutting portion extending upward as viewed in the figures (hereinafter simply referred to as "upward") is formed integrally with the movable lens frame 38 of the movable lens unit 32.

A sloping portion 40a serving as an abutted surface abutted by an abutting member 63 of an actuator 62 (described later) is formed running from front to rear and sloping down toward the rear lens group frame 36. Being inserted in a slotted portion 36a which is a guide slot formed in the rear lens group frame 36, the catcher rod 40 protrudes in such a way that the entire sloping portion 40a will be exposed from an outer peripheral portion of the rear lens group frame 36.

As described above, the movable lens unit 32 has its forward movement restricted, as the catcher rod 40 abuts the restricting portion 37a of the screw receiving tube 37. Also, the movable lens unit 32 has its backward movement restricted, as the catcher rod 40 abuts an adjustment ring 32a which is a restricting tube screwed over middle part of the outer peripheral portion of the rear lens group frame 36.

The adjustment ring 32a is a tubular member whose distal end face has been cut off obliquely into different lengths in the direction of the photographic optical axis O so that position at which a backward stroke of the movable lens unit 32 is restricted can be fine adjusted by rotating the movable lens unit 32 around the photographic optical axis O when the adjustment ring 32a is fixedly fitted over the rear lens group frame 36.

That is, thread grooves are formed in an inner peripheral surface of the adjustment ring 32a and screwed over thread grooves formed in an outer peripheral surface of the rear lens group frame 36. When turned around the direction of the photographic optical axis O, the adjustment ring 32a moves forward and backward along the photographic optical axis O in relation to the rear lens group frame 36, making it possible to fine adjust the backward stroke of the movable lens unit 32.

The movable lens unit 32 includes a compression coil spring 66 which is placed in parallel to the photographic optical axis O with proximal part housed in the catcher rod 40. The compression coil spring 66 is a pressing spring constituting an urging body which urges and thereby extends the movable lens unit 32 backward. Distal part of the compression coil spring 66 is housed in the restricting portion 37a of the screw receiving tube 37. In this way, the movable lens unit 32 is installed in the rear lens group frame 36, being constantly urged by the compression coil spring 66 so as to extend backward.

Starting from the distal end, the solid-state image pickup device unit 46 includes two optical members 42 and 43, a solid-state image pickup device chip 45 whose image area (not shown) is located in the front, and a TAB (Tape Automated Bonding) board 47, all of which are contained in the solid-state image pickup device holding frame 41. Incidentally, the solid-state image pickup device chip 45 and TAB board 47 are electrically interconnected via an integral FPC configuration.

The TAB board 47 has electronic components mounted on the topside and is connected with multiple communications lines of a cable 51 on the underside. The cable 51 is passed through the endoscope 2 and electrically connected with the video processor 4 via the universal cord 17, the scope cable 19, and the electrical connector 20 shown in FIG. 1. Distal part of the cable 51 is fitted over with a cable holding member 50 by thread bonding and clad by a cladding member 49 (described later) integrally with distal part of the cable holding member 50.

A reinforcement frame 48 is fitted on a proximal side of the solid-state image pickup device holding frame 41. The reinforcement frame 48 is covered by the cladding member 49 (described above) to the distal part of the cable 51, where the cladding member 49 is a heat-shrinkable tube which covers the cable holding member 50 integrally. Incidentally, in an interval between proximal part of the solid-state image pickup device holding frame 41 in which the solid-state image pickup device chip 45 is installed and the cable holding member 50, a space formed by the reinforcement frame 48 and cladding member 49 is filled with a protective agent such as an adhesive.

Also, an actuator holder 36b which holds the actuator 62 is formed in upper rear part of the rear lens group frame 36 so as to protrude upward, where the actuator 62 is a shape-memory alloy actuator device which moves the movable lens unit 32 forward and backward.

Next, a configuration of the actuator 62 installed on the image pickup unit 30 will be described with reference to FIGS. 3 to 8.

As shown in FIGS. 3 to 8, the actuator 62 mainly includes a rigid, long, guide tube 53 passed through the actuator holder 36b of the rear lens group frame 36; a shape-memory alloy wire 56 passed through the guide tube 53; a compression coil spring 57 passed through the guide tube 53 and fitted over the shape-memory alloy wire 56, the compression coil spring 57 being a pressing spring made of an elastic material and constituting an urging body; an insulating spring stopper tube 58 which is fitted into proximal part of the guide tube 53 while allowing a proximal half of the shape-memory alloy wire 56 to pass through, the insulating spring stopper tube 58 being an insulating tube; block bodies 59 which secure proximal ends of the shape-memory alloy wire 56 by crimping; a rod 64 which is passed through distal part of the guide tube 53 while allowing distal part of the shape-memory alloy wire 56 to pass through, the rod 64 being a tubular body; and an abutting member 63 fixedly attached to distal part of the rod 64 and having a bullet-shaped distal end.

Except for the distal part, the guide tube 53 is covered with a covering/cladding member 55 which is a heat-shrinkable tube. Furthermore, a U-shaped cover member 65 is fitted over the restricting portion 37a of the screw receiving tube 37 and actuator holder 36b of the rear lens group frame 36 so as to cover the catcher rod 40, rod 64, and abutting member 63 of the movable lens frame 38 (see FIGS. 5 to 8). Besides, outer peripheries of the restricting portion 37a and actuator holder 36b in a protruding direction are arc-shaped.

The shape-memory alloy wire 56 measures tens of microns in diameter, being made of shape memory alloys (hereinafter abbreviated to SMA) which contracts when heated and extends when cooled (left to cool to room temperature by itself). (Hereinafter the shape-memory alloy wire is referred to as an SMA wire.)

At distal end position, the guide tube 53 is placed flush with a distal end face of the actuator holder 36b and fixedly bonded to the actuator holder 36b. Also, the guide tube 53 is fitted precisely in the actuator holder 36b, being placed in parallel to the photographic optical axis O, so that a longitudinal axis of the guide tube 53 will satisfy optical characteristics (optical magnification) set for the image pickup unit 30.

The SMA wire 56 passed through the guide tube 53 and rod 64 turns back by penetrating a flank of the abutting member 63 (see FIGS. 4 and 8). As shown in FIG. 4, after being turned back at the abutting member 63, the SMA wire 56 is passed through an insulating tube 67. One end of the SMA wire 56 is fixedly crimped to a block body 59 and the other end is fixedly crimped to another block body 59.

The rod 64 is passed through the distal part of the guide tube 53 so as to be able to move forward and backward. With a distal end of the compression coil spring 57 abutted against a proximal end face of the rod 64, the rod 64 is urged forward together with the abutting member 63 installed at a distal end of the rod 64.

That is, the compression coil spring 57 fitted over the SMA wire 56 is placed between the rod 64 and insulating spring stopper tube 58 in the guide tube 53, with opposite ends of the compression coil spring 57 abutting the rod 64 and the insulating spring stopper tube 58, respectively. The compression coil spring 57, whose proximal end face abuts a distal end face of the fixed insulating spring stopper tube 58 and whose distal end abuts the proximal end face of the rod 64, urges the abutting member 63 forward together with the rod 64.

One of the block bodies 59 which secure both ends of the SMA wire 56 is larger in shape than bore diameter of the insulating spring stopper tube 58 and is placed in abutment with a proximal end face of the insulating spring stopper tube 58. The block body 59 is electrically connected to wires 60a of a supply cable 60 by soldering or the like. The other block body 59 is electrically connected to wires 60a of a return cable 60 by soldering or the like.

Connections between the block bodies 59 and cables 60 are kept insulated by being covered by the covering/cladding member 55 which covers the entire structure to the distal part of the guide tube 53. Incidentally, the cables 60 run to the scope connector 18 of the universal cord 17 of the endoscope 2 shown in FIG. 1 and current applied to the cable 60 is supplied from the video processor 4 via the scope cable 19.

As described above, the slotted portion 36a serving as a guide slot is formed, in upper front part of the rear lens group frame 36 as viewed in FIGS. 3 and 5 to allow the catcher rod 40 of the movable lens unit 32 to move straight forward and backward. The screw receiving tube 37 fitted over the rear lens group frame 36 restricts forward movement of the movable lens unit 32 by the proximal end face, as described above. In this case, the screw receiving tube 37 has the restricting portion 37a which defines a wide end position based on a distal end face of the catcher rod 40.

The adjustment ring 32a is fitted over the outer peripheral portion of the rear lens group frame 36 to restrict rearward extended position of the movable lens unit 32, thereby defining a tele end position based on a proximal end face of the catcher rod 40 in this case.

That is, forward extension of the movable lens unit 32 is restricted as the distal end face of the catcher rod 40 abuts a proximal end face of the restricting portion 37a. In this case, objective lenses establish optical characteristics (optical magnification) such that a viewing angle of the image pickup unit 30 will be set to a predetermined maximum wide angle. On the other hand, backward movement of the movable lens unit 32 is restricted as the proximal end face of the catcher rod 40 abuts a distal end face of the adjustment ring 32a. In this case, the objective lenses establish optical characteristics (optical magnification) such that the viewing angle of the image pickup unit 30 will be set to a predetermined maximum tele angle.

Also, when urged forward by the compression coil spring 57, the abutting member 63 installed at the distal end of the rod 64 of the actuator 62 abuts the sloping portion 40a of the catcher rod 40 which is an abutted member and thereby extends the movable lens unit 32 forward against backward urging force of the compression coil spring 66 on the distal side. The movable lens unit 32 stops at the wide end position when the distal end face of the catcher rod 40 abuts the proximal end face of the restricting portion 37a.

On the other hand, when current is applied to the SMA wire 56, the SMA wire 56 contracts due to temperature rises, hauling the abutting member 63 backward against forward urging force of the compression coil spring 57. Consequently, the abutting member 63 moves backward, separating from the sloping portion 40a of the catcher rod 40. Since the catcher rod 40 is urged backward by the compression coil spring 66 on the distal side, the movable lens unit 32 is extended backward. The movable lens unit 32 stops at the tele end position when the proximal end face of the catcher rod 40 abuts a distal end face of the adjustment ring 32a.

Also, the image pickup unit 30 according to the present embodiment is configured such that the movable lens unit 32 will be stopped only at the wide end position and tele end position by the actuator 62 to switch between two optical magnifications: an optical magnification of the wide mode and optical magnification of the tele mode.

Incidentally, the actuator 62 according to the present embodiment is configured such that extension and contraction of the SMA wire 56 will be controlled by shape-memory alloy resistance control circuit installed in the video processor 4, by controlling application of current to the SMA wire 56 in a conventional manner. The shape-memory alloy resistance control circuit has a conventional configuration, and thus description thereof will be omitted.

Next, configurations of the TAB board 47 installed in the solid-state image pickup device unit 46 of the image pickup unit 30 and the cable 51 connected to the TAB board 47 will be described with reference to FIGS. 9 to 11.

As shown in FIG. 9, the TAB board 47 has been cut in such a way that a connection portion 47a to be electrically connected to the solid-state image pickup device chip 45 will be narrowed on the distal side. In this way, the TAB board 47 is configured to secure a mounting area for electronic components to be mounted as well as to enable electrical connection with the solid-state image pickup device chip 45 which has been downsized.

The electronic components mounted on the TAB board 47 has been laid out so as not to fall off when bending stress is applied to the TAB board 47 which is flexible. Specifically, electronic components are arranged in multiple rows along a longitudinal direction of the TAB board 47 corresponding to the photographic optical axis O. Furthermore, on extensions to longitudinal lines or transverse lines passing between adjacent electronic components, other electronic components are placed to prevent the TAB board 47 from bending between the adjacent electronic components.

That is, electronic components are placed in rows or columns on extensions to those parts of the TAB board 47 which are prone to bending stress, being located between the adjacent electronic components. This makes the TAB board 47 resistant to deformation even if subjected to bending stress and thereby prevents the mounted electronic components from falling off.

Also, the electronic components are mounted on the TAB board 47 in such a way that the longitudinal direction of the electronic components will coincide with the longitudinal direction of the TAB board 47. This reduces width of the TAB board 47 and thus diameter of the solid-state image pickup device unit 46.

Furthermore, in accordance with the electronic components mounted on a front face of the TAB board 47, cable lands to be connected with various signal cables 51A including GND lines are provided on a rear face of the TAB board 47. Specifically, mainly digital electronic components and analog electronic components are mounted on the front face of the TAB board 47, and placement regions for the cable lands to be connected with the various signal cables 51A which transmit digital signals and analog signals are established on the back of the mounting regions of the electronic components (in locations to which the electronic components are projected).

This configuration makes it possible to reduce image noise, omission rates occurring when the various signal cables 51A are electrically connected to the cable lands by soldering or the like, and improper connections.

As shown in FIG. 11, various signal cables 51a to 51l (various signal cables 51A in FIGS. 9 and 10) are passed through the cable 51. Of the signal cables 51a to 51l, a signal cable 51a is a Vout cable and three signal cables 51h to 51j are digital signal cables.

The Vout cable 51a and three signal cables 51h to 51j are passed through the cable 51, being laid out as far apart as possible to prevent electromagnetic interference and reduce mutual noise interference.

The above-described image pickup unit 30 according to the present embodiment is fixedly fitted into the distal rigid member 24 which is a distal end body as shown in FIG. 13 when an end of the setscrew 27 screwed through the distal rigid member 24 presses against a recessed portion 37c which is a screw receiving portion formed in an outer peripheral surface of the screw receiving tube 37 shown in FIG. 12.

The screw-receiving recessed portion 37c is formed in the outer periphery of the screw receiving tube 37 near the rib 37b. That is, pressing force which is fixing force of the setscrew 27 prevents deformation of the screw receiving tube 37 due to radially inward strain. Also, the screw receiving tube 37 scatters the pressing force (fixing force) of the setscrew 27 to an inner end face of the rib 37b and to an inner peripheral surface on the near side of the rib 37b.

Since the rib 37b, which has a large wall thickness in a direction orthogonal to the photographic optical axis O, hardly deforms, the front lens group frame 34 is not loaded unduly. Also, since the pressing force of the setscrew 27 is scattered over the rear lens group frame 36, which is held in surface contact with an inner peripheral surface of the screw receiving tube 37, the rear lens group frame 36 is not loaded unduly.

Thus, since the screw receiving tube 37 with the setscrew 27 screwed through the distal rigid member 24 is fixedly fitted in the rear lens group frame 36 in which the movable lens unit 32 moves forward and backward, the pressing force (fixing force) of the setscrew 27 is not applied directly to the rear lens group frame 36 unlike in conventional cases. This reduces or prevents effects of strain deformation in the radially inward direction. Consequently, the image pickup unit 30 can prevent malfunctions in forward and backward movements of the movable lens unit 32 in the rear lens group frame 36.

That is, if the rear lens group frame 36 is deformed in the radially inward direction under strain, smooth forward and backward movements in the rear lens group frame 36 is obstructed because of increased contact friction between an outer peripheral portion of the movable lens frame 38 of the movable lens unit 32 and an inner peripheral surface of the rear lens group frame 36 or because the movable lens frame 38 gets stuck. Thus, to enable smooth forward and backward movements of the movable lens unit 32 by preventing radially inward deformation of the rear lens group frame 36, the image pickup unit 30 fixed to the distal rigid member 24 is configured such that the screw receiving tube 37 is interposed between the distal rigid member 24 and rear lens group frame 36.

Incidentally, as shown in FIG. 14, the screw receiving tube 37 may be configured as a simple tubular member instead of being equipped with the rib 37b (see FIG. 1), an outer peripheral surface of the front lens group frame 34 at maximum outside diameter and the outer peripheral surface of the rear lens group frame 36 may be placed integrally in surface contact with the inner peripheral surface of the screw receiving tube 37. In that case, preferably the screw-receiving recessed portion 37c of the screw receiving tube 37 is formed near the maximum outside diameter of the front lens group frame 34.

Next, the forward and backward movements of the movable lens unit 32 will be described in detail mainly with reference to FIGS. 15 to 17, illustrating how the movable lens unit 32 in the rear lens group frame 36 is extended forward and backward by the actuator 62 of the image pickup unit 30, and especially how the movable lens unit 32 is extended forward from the tele end position on the rear side to the wide end position.

In the image pickup unit 30, when the movable lens unit 32 remains stopped at the tele end position, current is being applied to the SMA wire 56 in the actuator 62. The SMA wire 56, which contracts due to temperature rises by the application of the current, is hauling the rod 64 backward together with the abutting member 63 against the urging force of the compression coil spring 57. In this state, since the abutting member 63 of the actuator 62 is out of contact with the catcher rod 40 of the movable lens frame 38, the movable lens unit 32 remains stopped in abutment with the adjustment ring 32a, being urged backward by the compression coil spring 66.

In this state of tele mode, when the current stops being applied to the SMA wire 56 of the actuator 62, the SMA wire 56 cools by itself and extends to its initial length. Consequently, as shown in FIG. 16, the abutting member 63 is moved forward together with the rod 64 of the actuator 62 by the compression coil spring 57 which urges the rod 64 forward.

After being moved forward, the abutting member 63 comes into contact with the sloping portion 40a of the catcher rod 40 on the movable lens frame 38 and presses the entire movable lens unit 32 so as to extend the movable lens unit 32 forward along the photographic optical axis O in the rear lens group frame 36 against the compression coil spring which urges the movable lens unit 32 forward, as shown in FIGS. 15 and 17.

Also, when a spherical surface of the bullet-shaped abutting member 63 extends the entire movable lens unit 32 forward by abutting the sloping portion 40a of the catcher rod 40, the pressing force (stress) is scattered in an X-axis direction which corresponds to the forward direction and in a Y-axis direction which corresponds to a downward direction as viewed in FIG. 17, i.e., a direction approximately orthogonal to the photographic optical axis O, exerting a stress F in a direction approximately 45 degrees to the lower left of FIG. 17.

When the distal end face of the catcher rod 40 abuts the proximal end face of the restricting portion 37a, the movable lens unit 32 stops with its forward movement restricted. In this state, the objective lenses according to the present embodiment establish optical characteristics (optical magnification) such that a viewing angle of the image pickup unit 30 will be set to a predetermined maximum wide angle.

Even when the movable lens unit 32 is stopped at the wide end position, the spherical surface of the abutting member 63 abuts and presses the sloping portion 40a of the catcher rod 40 forward and the stress F is constantly applied to the movable lens unit 32 in the direction approximately 45 degrees to the lower left of FIG. 17. That is, the movable lens unit 32 of the image pickup unit 30 stops at the wide end position, being constantly pressed in the X-axis direction which corresponds to the forward direction and Y-axis direction which corresponds to the downward direction in this case.

In this way, with the image pickup unit 30 according to the present embodiment, even if there is a loose fit between the movable lens frame 38 of the movable lens unit 32 and the rear lens group frame 36 which is a fixed lens frame, the movable lens unit 32 can stably stop at a position—the wide end position in this case—which satisfies desired optical characteristics. Consequently, even if manufacturing accuracy of the movable lens frame 38 and rear lens group frame 36 is not very high, the movable lens unit 32 can stably stop at the predetermined wide end position. This provides the advantage of increased yields.

Furthermore, even if there is a loose fit between the movable lens frame 38 and rear lens group frame 36, since the movable lens unit 32 moves by being constantly pressed in the forward direction (X-axis direction) and a radially outward direction approximately orthogonal to the photographic optical axis O (Y-axis direction orthogonal to the X-axis direction which is parallel to the photographic optical axis O; downward direction in FIG. 17 in this case), the image pickup unit 30 can prevent images from jittering during forward and backward movements. In this way, since the movable lens unit 32 is constantly stressed in the forward direction and one radially outward direction, when the movable lens unit 32 is extended forward, the image pickup unit 30 can stop the movable lens unit 32 at a desired wide end position in the endoscope 2 which is used in all attitudes. Thus, the image pickup unit 30 can stably reproduce a desired optical magnification (wide zoom).

The reason why reproducibility of the movable lens unit 32 is improved only during wide zooming as described above is that the image pickup unit 30 requires, in particular, accuracy in wide end stop position of the movable lens unit 32, i.e., the wide end stop position where the viewing angle becomes large. That is, the image pickup unit 30 according to the present embodiment can be configured to improve reproducibility of the stop position of the movable lens unit 32 during wide zooming in which the viewing angle becomes large and prevent vignetting.

Thus, the image pickup unit 30 according to the present embodiment can be reliably fixed to the distal rigid member 24 which is a distal end body without obstructing slidability of the movable lens unit 32 equipped with the movable lens frame 38 which moves forward and backward and can enable improved manufacturing yields and improved reproducibility with which the movable lens unit 32 can be stopped at a predetermined wide end position.

Incidentally, although the sloping portion 40a of the catcher rod 40 on the movable lens frame 38 may be planar, alternatively the sloping portion 40a of the catcher rod 40 may have a recessed shape with an arc-shaped cross section as shown in FIG. 18 to prevent misalignment of the abutting member 63 which has a spherical surface on a distal side and ensure abutment. Furthermore, the sloping portion 40a of the catcher rod 40 may have a recessed shape with a V-shaped cross section as shown in FIG. 19 to reduce contact friction with the abutting member 63, or a recessed shape with a trapezoidal cross section as shown in FIG. 20. Besides, the sloping portion 40a of the catcher rod 40 may have an arc-shaped longitudinal section which curves outward with decreasing distance from the distal end as shown in FIG. 21.

The bullet-shaped distal end face of the abutting member 63 is made spherical to further reduce contact friction with the sloping portion 40a which can have any of various sectional shapes.

Also, as shown in FIG. 22, a leaf spring 70 may be installed at the distal end of the rod 64 to constantly press the movable lens unit 32 in the forward direction (X-axis direction) and one radially outward direction (Y-axis direction orthogonal to the X-axis direction which is parallel to the photographic optical axis O; downward direction in FIG. 22 in this case).

Specifically, the leaf spring 70 has an arc shape which curves away from the movable lens frame 38. An arcuate surface at a distal end of the arc shape abuts a rear corner portion of the catcher rod 40 of the movable lens frame 38, constantly pressing the movable lens unit 32 in the forward direction and one radially outward direction. Incidentally, no sloping portion 40a is formed on the catcher rod 40. Instead, an arcuate surface 40b is formed on the corner portion abutted by the leaf spring 70.

As shown in FIGS. 15 to 17, the movable lens frame 38 of the movable lens unit 32 according to the present embodiment has protruding portions 38a formed at opposite ends around the outer peripheral portion. That is, since the movable lens frame 38 slides in the rear lens group frame 36, the protruding portions 38a are formed at opposite ends around the outer peripheral portion to reduce a contact area with the inner peripheral surface of the rear lens group frame 36 and thereby reduce friction during forward and backward movements of the movable lens unit 32.

Instead of the protruding portions 38a, as shown in FIG. 23, in the direction in which the stress F is applied by the movable lens frame 38, i.e., on a lower side of the outer peripheral portion in this case, multiple protrusions 38b (only two protrusions are shown in FIG. 23) may be formed at axisymmetric positions with respect to a line passing through the photographic optical axis O and parallel to the Y-axis in FIG. 23 so that the movable lens unit 32 can move forward and backward smoothly in the rear lens group frame 36.

Preferably the protrusions 38b on the movable lens frame 38 shown in FIG. 23 are shaped to come substantially into point contact with the inner peripheral surface of the rear lens group frame 36 at such positions that will allow the movable lens frame 38 to move forward and backward stably in the rear lens group frame 36.

Also, as shown in FIG. 24, in the direction in which the stress F is applied by the rear lens group frame 36, i.e., on a lower side of the inner peripheral surface in this case, two flat portions 36c may be formed at axisymmetric positions with respect to a line passing through the photographic optical axis O and parallel to the Y-axis.

Being formed in the longitudinal direction, the flat portions 36c on the rear lens group frame 36 in FIG. 24 are placed in line contact with outer peripheral portion of the movable lens frame 38, making it possible to reduce friction during forward and backward movements of the movable lens unit 32.

Incidentally, although in the present embodiment, the actuator 62 moves the movable lens unit 32 forward using the SMA wire 56 as drive means, this is not restrictive and the actuator 62 may use other drive means which moves the movable lens unit 32 forward along the photographic optical axis O.

Also, although in the image pickup unit 30 according to the present embodiment, the position at which the movable lens unit 32 stops after moving forward is designated as a wide end position, it is not limited to this and the position at which the movable lens unit 32 stops after being moved backward by the actuator 62 may be designated as the wide end position.

In other words, the direction in which the movable lens unit 32 is urged by the compression coil spring 66 which is an urging member and the drive direction in which the movable lens unit 32 is extended by the actuator 62 may be set by reversing the forward and backward directions along the photographic optical axis O according to the embodiment described above.

That is, the direction in which the movable lens unit 32 is urged by the compression coil spring 66 and the direction in which the movable lens unit 32 is extended by the actuator 62 are relative and may be reversed as long as the movable lens unit 32 is constantly stressed in one radially outward direction at the wide end position according to predetermined optical characteristics and is able to stop at the desired wide end position in the endoscope 2 which is used in all attitudes, making it possible to stably reproduce a desired optical magnification (wide zoom).

The present invention can implement an endoscopic image pickup unit which can be reliably fixed to a distal end body without obstructing slidability of a movable lens frame which moves forward and backward and can enable improved manufacturing yields and improved reproducibility with which the movable lens frame can be stopped at a predetermined wide end position.

The invention described above by way of the embodiment is not limited to the embodiment and variations thereof. Numerous variations can be made at implementation levels without departing from the spirit of the present invention. Furthermore, the above embodiment includes inventions at various stages, and various inventions can result from proper combinations of multiple components disclosed herein.

For example, even if some of the components of the embodiment are removed, as long as the problems to be solved by the invention can be solved and the advantages of the invention are available, the resulting configuration can constitute an invention.

The endoscopic image pickup unit according to the present invention described above has the following features.

(Annex 1)

An endoscopic image pickup unit which, being fixedly fitted in a distal end body of an endoscope by a fixing member, can change optical characteristics of an objective optical system, the endoscopic image pickup unit comprising:

a first fixed lens frame which holds a first objective lens group;

a second fixed lens frame which, being fitted over the first fixed lens frame, holds a second objective lens group;

a movable lens frame which, being installed in the second fixed lens frame so as to be able to move forward and backward along a photographic optical axis, holds a movable lens;

an urging member which urges the movable lens frame in one direction along the photographic optical axis;

an actuator which extends the movable lens frame in the other direction along the photographic optical axis against urging force of the urging member;

an abutting member which, being installed on the actuator, abuts the movable lens frame;

an abutted portion which, being installed on the movable lens frame, is abutted by the abutting member; and an abutted surface which, being formed on the abutted portion, scatters pressing force applied by the abutting member, in a direction approximately orthogonal to the photographic optical axis.

(Annex 2)

The endoscopic image pickup unit according to annex 1, wherein the abutted surface is a slope formed on the movable lens frame.

(Annex 3)

The endoscopic image pickup unit according to annex 1 or 2, wherein the abutting member has a spherical surface which abuts the abutted surface.

(Annex 4)

The endoscopic image pickup unit according to any one of annexes 1 to 3, wherein an optical magnification for a maximum wide zoom is established at a position where the movable lens frame stops after moving by being extended in the other direction by the actuator.

What is claimed is:

1. An endoscopic image pickup unit which, being fixedly fitted in a distal end body of an endoscope by a fixing member, can change optical characteristics of an objective optical system, the endoscopic image pickup unit comprising:

a first fixed lens frame which holds a first objective lens group;

a second fixed lens frame which holds a second objective lens group;

a movable lens frame which, being installed in the second fixed lens frame so as to be able to move forward and backward along a photographic optical axis, holds a movable lens;

an urging member which urges the movable lens frame in a first direction along the photographic optical axis;

an actuator which extends the movable lens frame in a second direction along the photographic optical axis against urging force of the urging member;

wherein the actuator includes at least;

an abutting member; and an urging body configured to urge the abutting member in the second direction along the photographic optical axis, the second direction being opposite to the first direction; and wherein the movable lens frame includes an abutted surface which is configured to be in contact with the abutting member, wherein, when the abutting member which is urged in the second direction by the urging body comes in contact with the abutted surface and thereby a pressing force is applied to the abutted surface, the abutted surface is configured to distribute the pressing force applied by the abutting member in a third direction approximately orthogonal to the photographic optical axis and in the second direction along the photographic optical axis, wherein the movable lens frame is extended in the second direction along the photographic optical axis in a state of being pressed in the third direction approximately orthogonal to the photographic optical axis.

2. The endoscopic image pickup unit according to claim 1, wherein the abutted surface is a slope formed on the movable lens frame.

3. The endoscopic image pickup unit according to claim 1, wherein the abutting member has a spherical surface which comes in contact with the abutted surface.

4. The endoscopic image pickup unit according to claim 1, wherein an optical magnification for a maximum wide zoom is established at a position where the movable lens frame stops after moving by being extended in the second direction by the actuator.

5. The endoscopic image pickup unit according to claim 1, wherein the actuator further includes a shape memory alloy wire which contracts in the first direction by electric current application and thereby moves the abutting member in the first direction against the urging force of the urging body, and the abutting member is urged in the second direction by the urging body when the shape-memory alloy wire expands in the second direction by a stop of the electric current application.

6. The endoscopic image pickup unit according to claim 1, wherein the actuator further includes:

a driving source which generates a driving force in the first direction and move the abutting member in the first direction by the driving force against the urging force of the urging body, and wherein the abutting member is urged in the second direction by the urging body when the generation of the driving force by the driving source is stopped.

7. The endoscopic image pickup unit according to claim 1, wherein the abutted surface is formed on an abutted portion formed integrally with the movable lens frame.

* * * * *